United States Patent [19]

Török et al.

[11] Patent Number: 5,042,503
[45] Date of Patent: Aug. 27, 1991

[54] PROCESS AND APPARATUS FOR EXTENDED, NON-INVASIVE MONITORING OF UTERINE CONTRACTIONS

[75] Inventors: Miklós Török; János Bóta, both of Budapest; Imre Bartos, Budaörs, all of Hungary

[73] Assignee: Kisszövetkezet Mikroker, Budapest, Hungary

[21] Appl. No.: 483,206

[22] Filed: Feb. 20, 1990

Related U.S. Application Data

[63] Continuation-in-part of Ser. No. 133,937, Dec. 17, 1987, abandoned, and a continuation-in-part of Ser. No. 238,318, Aug. 30, 1988, abandoned.

[51] Int. Cl.$^5$ .............................................. A61B 5/11
[52] U.S. Cl. ................................. 128/775; 128/778; 128/782
[58] Field of Search ............... 128/710, 721, 775, 780, 128/782, 778, 697, 698

[56] References Cited

U.S. PATENT DOCUMENTS

| Re. 31,158 | 2/1983 | Carter et al. | 128/778 |
| 3,989,034 | 11/1976 | Hojaiban | 128/698 |
| 4,624,263 | 11/1986 | Slavin | 128/710 |
| 4,738,268 | 4/1988 | Kipnis | 128/777 |

FOREIGN PATENT DOCUMENTS

| 0140418 | 3/1980 | Fed. Rep. of Germany | 128/788 |
| 8603115 | 6/1986 | PCT Int'l Appl. | 128/775 |
| 8701573 | 3/1987 | PCT Int'l Appl. | 128/775 |
| 786982 | 12/1980 | U.S.S.R. | 128/775 |
| 1074483 | 2/1984 | U.S.S.R. | 128/788 |
| 1243692 | 7/1986 | U.S.S.R. | 128/788 |

OTHER PUBLICATIONS

Hughes et al., "On-Line Digital Processing of Uterine Contraction Waveforms", Naecon '77 Record, (1977), pp. 244-250.
Lin et al., "A Microprocessor-Based Data Acquisition and Processing System", Proceedings of IEEE, vol. 65, No. 5, (1977), pp. 722-729.

Primary Examiner—Lee S. Cohen
Assistant Examiner—John D. Zele
Attorney, Agent, or Firm—Schweitzer Cornman & Gross

[57] ABSTRACT

A process and apparatus is disclosed for effective home monitoring of uterine contractions of a pregnant woman, in order to provide early warning signs of possible premature birth. Using a transducer of known type, uterine contractions are monitored continuously over a period of time. An electrical signal is generated, which is digitized for processing with simple IC chips. Importantly, only those contractions whose intensity exceeds a threshold value for a duration exceeding a threshold period are stored for future processing and analysis. Analysis of these over-threshold values provides a valuable basis on which to judge the likelihood of premature birth. Limiting the analysis only to such over-threshold values enables the system and equipment to be of a highly simplified, economical construction, suitable for widespread home use yet capable of monitoring over an extended duration. Among other features, if the number of over-threshold (both intensity and duration) exceeds a predetermined value in a given period of time, an alarm signal is given, indicating that the patient's condition should be evaluated by medical specialist.

8 Claims, 3 Drawing Sheets

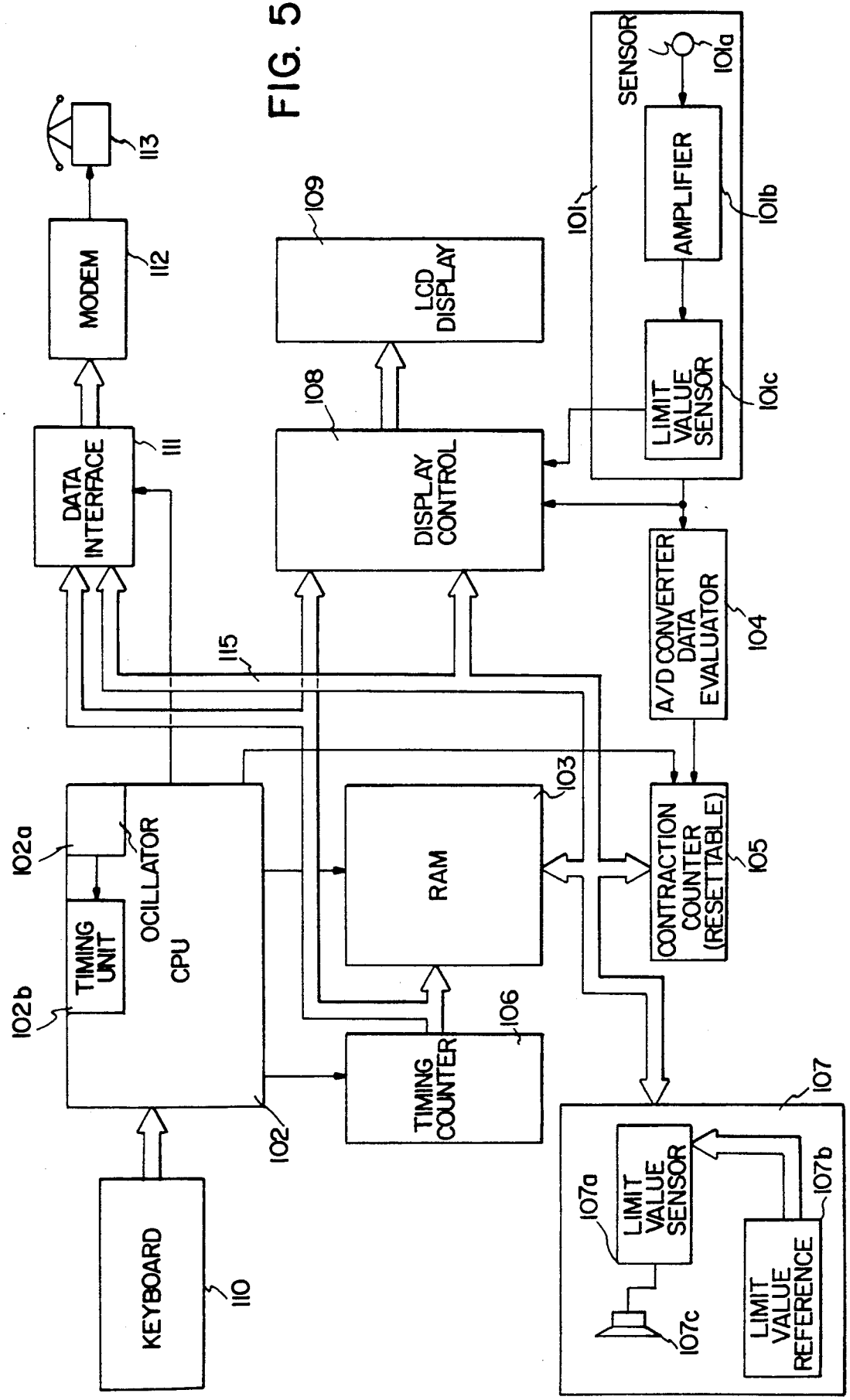

PROCESS AND APPARATUS FOR EXTENDED, NON-INVASIVE MONITORING OF UTERINE CONTRACTIONS

RELATED APPLICATIONS

This application is a continuation-in-part of our earlier application Ser. No. 133,937, filed Dec. 17, 1987 and application Ser. No. 238,318, filed Aug. 30, 1988, both now abandoned, the disclosures of which are incorporated by reference.

BACKGROUND AND SUMMARY OF THE INVENTION

The invention relates to a process, and related apparatus, for external measurement and analysis of uterine contractions, particularly for early indications of impending premature birth.

Reducing the mortality rate of new-born infants is a significant obstetric problem. In this respect, it has been observed that the great majority of early infant deaths is the result of premature birth, with the infants being born in premature condition, with low body weight. In many cases, even with extraordinary dedication of personnel and resources, it is not possible to save many prematurely born infants. For this reason, significant efforts have been focused on preventing such premature births.

It is well known that contractions of the uterus can be detected to occur throughout the whole time of a pregnancy. As described in detail by M. Katz, P. J. Gill and R. B. Newman in the American Journal of Obstetrics and Gynecology, 1986, Issue No. 154, significant differences can be detected in the intensity and frequency of uterine contractions between groups of pregnant women giving normal birth in due course and those whose pregnancies end in premature birth. The frequency and intensity of uterine retractions throughout much of the period of pregnancy in the latter group of women are considerably higher than in the case of women who give birth in the normal course. It is also well established that the activity of the uterus several days prior to birth becomes significantly stronger, giving an early warning of the probable start of the birth. If detected in time, these early warning indications can be responded to, to ward off otherwise premature birth.

A well known means for the measurement of uterine contraction activity utilizes a pressure sensing device which is strapped on to the abdominal wall of the pregnant woman. Uterine contraction activity is detected by a pressure sensing transducer, which generates an electrical signal capable of being evaluated by a gynecological specialist. Principally, these apparatuses are somewhat large and cumbersome, and are available only for clinical use under medical supervision. Necessarily, the observation time is relatively short, and the facilities is not available to large numbers of expectant mothers.

An improvement in the above system is described by M. Katz and P. J. Gill in the American Journal of Obstetrics and Gynecology, 1986, Issue No. 66. The described instrument is portable and can be used in the home of the patient. It consists of a traditional pressure sensing unit which is arranged to record uterine activity over a period of about 200 minutes. The data sensed during the observation interval is stored, and then transmitted via modem and telephone to the medical specialist. If necessary, the patient is advised to come in for observation. A major disadvantage of this arrangement is that it requires a rather highly developed infrastructure, an efficiently functioning telephone network, and permanent 24 hour monitoring by the medical facility. Although the instrument is portable, its size is relatively large, and the modem/transmitter arrangement and the evaluating receiver are required parts of the system, making it somewhat complicated and costly.

The present invention is directed to a new procedure, and to related apparatus, which may be made available on a large scale basis for home use by pregnant women for the monitoring of uterine contraction activity. The procedure of the invention is based upon the recognition that effective monitoring, for early detection of possible premature birth, requires a relatively high degree of continuity in the monitoring. Further, in order to provide a high degree of universality and acceptability, the procedure must be relatively simple, comfortable, economical and effective.

The procedure and apparatus of the invention take advantage of our observation that impending premature birth can be recognized by the occurrence of uterine contractions of an intensity level and duration in excess of a predetermined threshold, occurring at a frequency greater than a predetermined number per unit of time. Accordingly, the procedure of the invention does not have to rely upon a continuous measurement and storage of the data to frequency and intensity of uterine contractions. Rather, it ignores those contractions of a lower than threshold intensity, and of shorter duration than a predetermined time. With respect to those contractions whose intensity and duration exceed the threshold limits, the procedure of the invention makes no effort to record for later evaluation either the intensity or the duration of such contractions, but rather simply in effect indexes a counter registering the fact that such a contraction did occur, and records the time of its occurrence.

Pursuant to the procedure of the invention, vast amounts of significant information are distilled to a few items of data, which is stored for evaluation. The data stored is simply the number of contractions exceeding the threshold values and the times when such contractions occurred. If the number of registered contractions in a given period of time, for example, in excess of four or five per hour, an audible alarm can be sounded, so that the patient knows to get in touch with her medical adviser. Where desired, the stored data can be downloaded into the medical adviser's system for more detailed analysis.

Because the procedure of the invention requires the storage of only a minimum amount of data, it is possible for a simple, low cost home device, utilizing simple IC chips, to enable extended monitoring of the patient. This provides for a greatly increased degree of probability that an impending premature birth may be detected in time to be avoided by proper medication and treatment. For example, even a simple device according to the invention, and utilizing the above described procedure, can be used to measure uterine contractions continuously for a period of at least 24 hours. At the end of such period, the data can be downloaded, if desired, or the device can simply be reset for a subsequent period of monitoring. Depending upon the anticipated likelihood of premature birth with a given expectant mother, the device may be used on a periodic basis, within the same total limits of its data storage capacity. For example, rather than continuous monitoring for 24 hours, the device may be used in daily three hour periods over a span of eight days, or, for example, in daily one hour periods over a span of 24 days. When the device is used in the periodic manner, continuous monitoring may obviously be initiated at any time that the periodically monitored data indicated a potential problem.

For a more complete understanding of the above and other features and advantages of the invention, reference should be made to the following detailed description of preferred embodiments of the invention and to the accompanying drawing.

DESCRIPTION OF THE DRAWINGS

FIG. 5 is a block diagram of a modified version of the apparatus of the invention.

DESCRIPTION OF PREFERRED EMBODIMENTS

In a simple system for carrying the process of the invention, a pressure sensing transducer is mounted to sense uterine contractions of an expectant mother. Many of these contractions, it should be noted, are not felt by the mother herself, but nevertheless can be sensed by the pressure transducer, in accordance with known techniques. As uterine contractions occur, an analog output voltage, corresponding to the intensity of the contractions, is generated by the pressure sensing transducer. Typically, this is a low level voltage which is suitably amplified. When the voltage exceeds a threshold level, reflecting a contraction of significant intensity, a timing period is commenced. Thereafter, when the contraction ceases to be of greater than threshold intensity, the timing is ended, and the duration of over-threshold contraction is compared to a predetermined time value, which typically may be in the range of 30 to 300 seconds.

If, and only if, there is an over-threshold intensity for a given duration, is the event recorded, along with the time of its occurrence. Since only "significant" contractions are recorded, most of the data which is sensed and processed is simply discarded, and it thus takes up none of the memory capacity of the device.

Significantly, the number of recorded, over-threshold contractions over a given time period, usually one hour, is evaluated. If a predetermined minimum number is exceeded, this is regarded as a circumstance meriting immediate medical evaluation, and an alarm device, advantageously a sound device is actuated. The procedure is both simple and efficient, easily carried out at home by the pregnant woman, yet is highly effective as a means of providing early warning against premature birth. Given the detection of early warning symptoms, it is often possible to provide appropriate treatment and/or medication to the mother, to extend the pregnancy.

Figure 1:
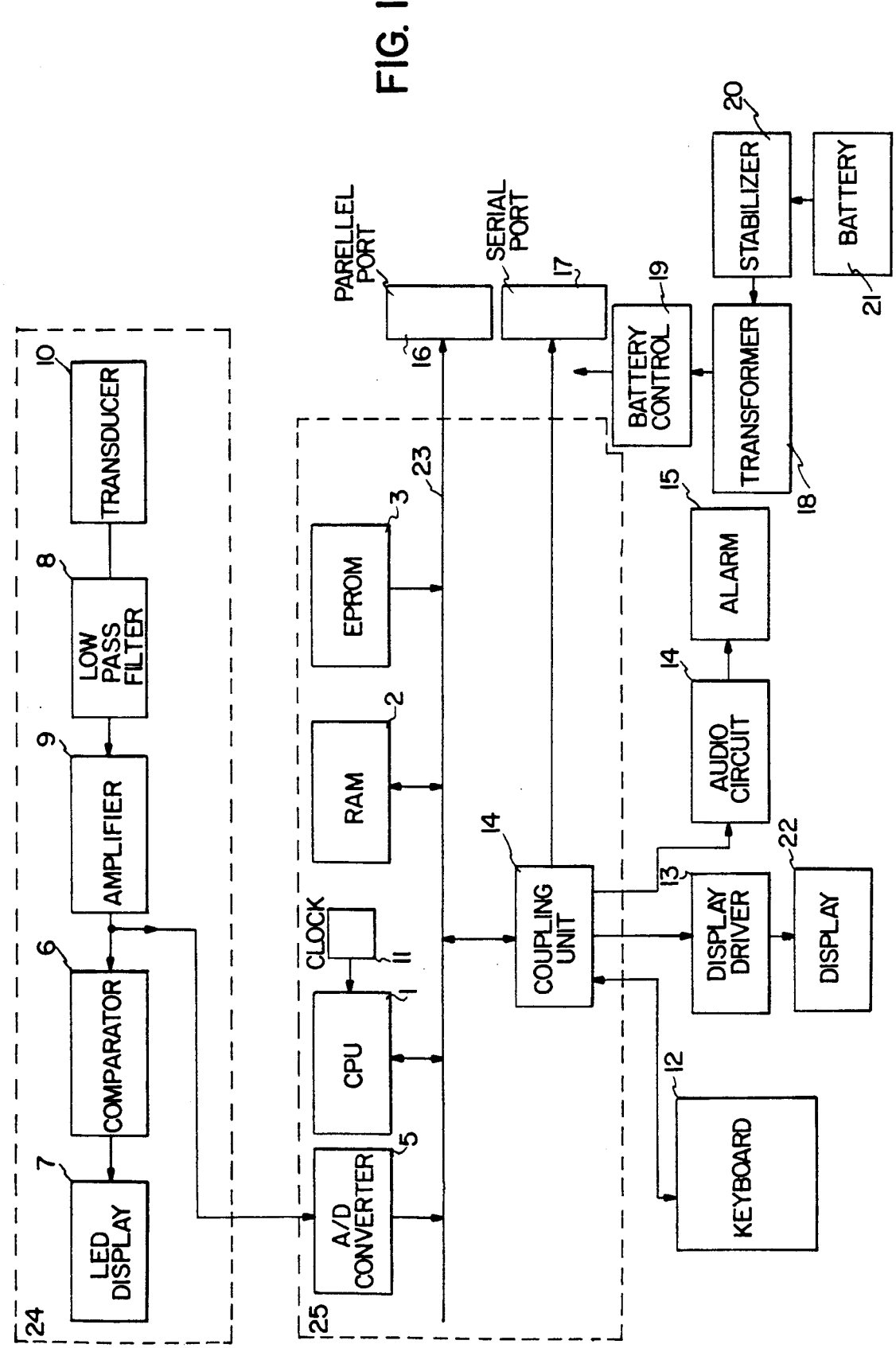
FIG. 1 is a highly simplified block circuit diagram of a simple apparatus for carrying out the process of the invention.

With reference initially to FIG. 1, the reference numeral 24 designates generally an analog sensing section of a monitoring device, while the numeral 25 designates generally a control section. The sensing section includes a pressure sensing transducer 10, which may be of a well known type, arranged to produce an electrical signal in proportion to the pressure sensed thereby. The output of the pressuring sensing transducer 10 is passed through a low-pass filter 8, to block extraneous signals, and is then passed through an amplifier 9. The output of the amplifier 9 is directed to an analog-to-digital (A/D) converter 5, which converts the analog signal to digital form for processing in the processing unit 25. The output of the amplifier 9 is also directed through a comparator 6 to an LED display section 7, which comprises two LED units "LLV" and "ULV" (see FIG. 2), arranged to be lit respectively when the output signal of the amplifier is below the lower limit value or above the upper limit value. The function of these will be further explained hereinafter.

The A/D converter 5 has an eight bit digital output, which is connected to the internal system bus 23 of the processing unit 25.

In the system of FIG. 1, the processing unit 25 includes a CPU 1, with an associated clock signal circuit 11. A random access memory (RAM) 2 is connected to the bus. Typically, the RAM may be of 16 Kb capacity. There is also a 16 Kb capacity EPROM 3, which incorporates the pre-programmed routines and permanent memory storage, and a coupling unit 4. Desirably, these circuit elements are CMOS units. NSC 800, NSC 810, NSC 830 type integrated circuits can be used to advantage for the CPU 1, clock circuit 11, and coupling unit 4.

The coupling unit 4 is advantageously connected to a simple keyboard 12 or switch bank, providing for limited user input. Also connected to the coupling unit is a display output 22, communicating through a display driver 13, and a miniature sound (alarm) transmitter 15, connected through an audio frequency circuit 14. To advantage, the keyboard 12 may be a foil-type board. The display 22 may advantageously comprise a 7 by 7 LCD display. The device may also include serial and parallel ports 16, 17 for downloading of data, programming of the EPROM, etc. The serial output advantageously includes an RS-232 coupling. The circuit can be driven by means of a rechargeable battery 21 connected through a stabilizing unit 20, voltage transformer 18 and battery control circuit 19.

Figure 4:
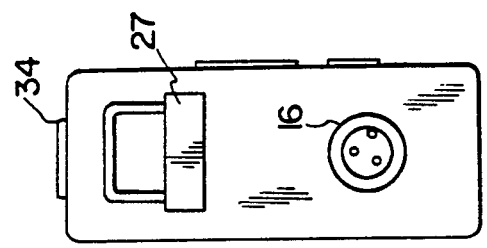
FIG. 4 is an end elevational view of the device of FIG. 2.
Figure 2:
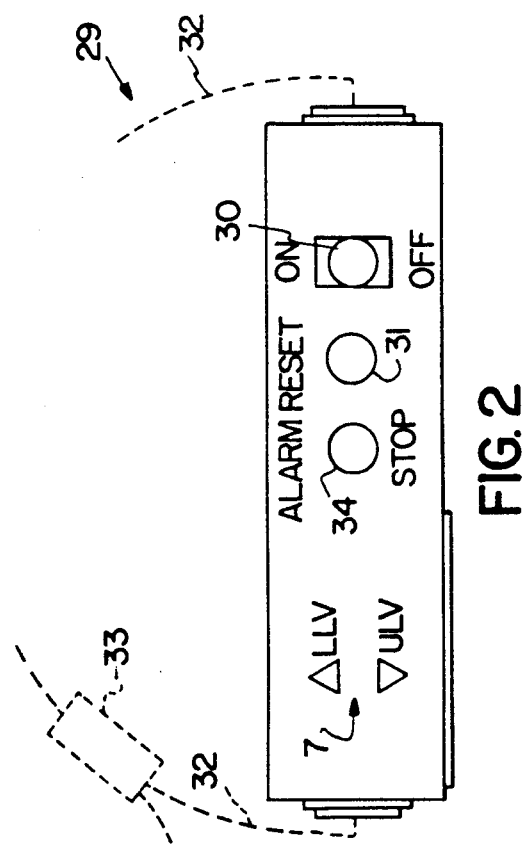
FIG. 2 is a top plan view of a monitoring device according to the invention.
Figure 3:
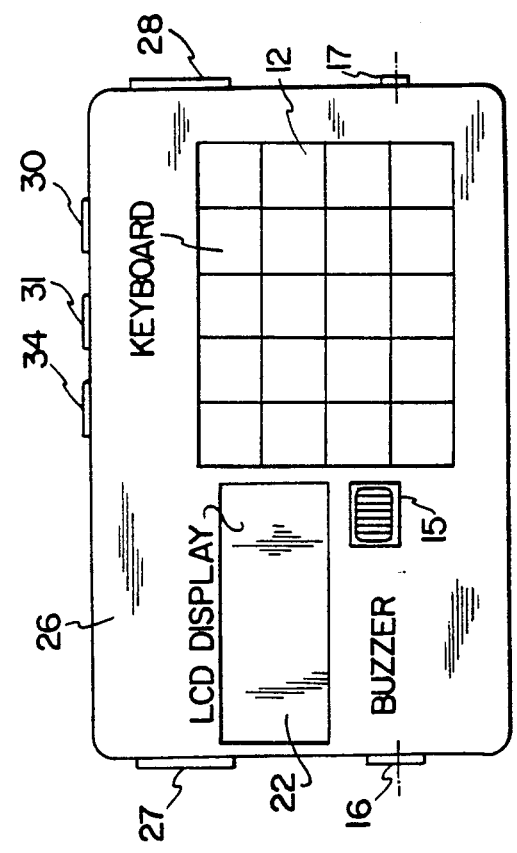
FIG. 3 is a front elevational view of the device of FIG. 2.

An advantageous mechanical makeup of the apparatus of the invention is shown in FIGS. 2-4. There is shown there a molded instrument casing 26, preferably of a suitable plastic material. Openings are provided in the front of the instrument casing for the LCD display 22, the foil keyboard 12 and the sound alarm 15. The pressure sensing transducer 10 (not visible in FIGS. 2-4) is mounted on the back face of the instrument casing, facing the body of the woman. A mounting strap, schematically indicated at 29 in FIG. 2 and comprising strap sections 32, is attached to the instrument at opposite ends 27, 28. The strap sections 32 include an adjustment feature 33 by means of which the pressure of the instrument casing against the abdomen may be controlled.

At opposite ends of the casing are the input/output connections 16, 17. Along the top face, visible in FIG. 2, are the two LED elements "LLV" and "ULV", comprising the LED display 7. These are arranged to be easily visible to the wearer. Also provided along the top wall of the casing are an on/off switch 30, a reset/start button 31 and an alarm stop switch button 34.

The device of FIGS. 1-4 is used in the following manner: Initially, the instrument casing is placed on the abdomen of the pregnant woman, and the switch 30 is turned to the "on" position. The mounting strap 29 is then adjusted for tightness until neither of the LED display lights "LLV" or "ULV" is lighted. This signifies that the initial pressure on the transducer 10 is above the lower limit value, but still below the upper limit value. The device is now ready to be used, and a monitoring period is commenced by pressing the start/reset button 31.

As time passes, a generally continuous DC voltage is produced by the sensor 10, and this voltage signal changes very slowly as a function of the intensity of uterine contraction activity. The low-pass filter 8 removes extraneous signals, and the passed signals are amplified to a level suitable for the A/D converter 5. In the converter 5, the incoming signal is periodically sampled and digitized. Data are selected for "permanent" storage where the intensity of the contraction exceeds a predetermined threshold value and the duration exceeds a predetermined time, which may be preset to, for example 30 seconds up to 300 seconds. The data stored can consist simply of the times of occurrence of the selected contractions.

Periodically, and this may be performed at the end of predetermined sampling periods, the stored data of significant contractions is examined for evaluation of times of occurrence. Experience has indicated that, in the case of more than four "significant" uterine contractions per hour is cause for concern and an indication that medical evaluation is needed. Accordingly, if an examination of the stored events indicates more than four such events within the most recent hourly period, the audible alarm 15 is sounded. Desirably, this will continue until turned off by the user via the alarm stop button 34.

The stored data may be reviewed in the display 22, or it may be downloaded to the physician, either at the physician's office or over the telephone through the serial port 16.

In the initial set-up of the device on the patient, the preliminary indications of the patient, if any, are evaluated to determine the particular program to employ i.e. whether to have the apparatus operate continuously, or in three hour or one hour segments daily, for example.

FIG. 5 shows an alternative circuit used in carrying out the processes of the invention. The system is arranged to sample data in predetermined time segments, such as one hour intervals. During the sampling interval, the significant uterine contractions are simply counted. At the end of the sampling period, the number of the count and the data indicating the hourly period are stored in RAM. They can simultaneously be displayed and/or downloaded. Where the number of significant contractions for the hourly period is above the predetermined value (for example above four contractions per hour) an audible alarm is sounded.

In the system of FIG. 5, a CPU 102 is provided, which includes an oscillator 102a and timing unit 102b. A keyboard or other input device 110 is provided for control and operations of the CPU. The CPU controls the operation of the timing counter 106, the RAM unit 103, and RS-232 unit 111 and a contraction counter unit 105.

An analog sensing unit 101 incorporated in the system of FIG. 5 includes a pressure sensing transducer 101a, an associated amplifier 101b and a limit value sensor 101c. The limit value sensor will pass only those signals above a threshold value.

The principal output of the limit value sensor 101c is connected to a circuit 104 which includes an A/D converter for digitizing the signal from the analog unit, and a data evaluation circuit for evaluating the digitized signals in terms of intensity and duration. To this end, the data evaluation circuit includes a monostable multivibrator, which receives the input from the limit value sensor 101c, a differentiating circuit having its input connected to the multivibrator, and a NAND gate whose inputs are connected to the output of the differentiating circuit and the input of the monostable multivibrator. The input of the monostable multivibrator receives the signal from the limit value sensor 101c, and the output of the data evaluation unit is formed by the output of the NAND gate. When the signal supplied to the limit value sensor exceeds a threshold limit, it is passed to the A/D converter, and data evaluation circuit. If the signal persists for a sufficient time period to be characterized as a uterine contraction, determination of such signal triggers an output of the data evaluation unit to the contraction counter 105. The contraction counter simply accumulates the number of "significant" contractions that occur during the sampling period. While this counting is underway, it can be monitored via an LCD display unit 109, driven by a display control 108 connected to an internal bus 115.

At the end of the one hour sampling period, the timing data from the unit 102 is loaded into the memory address of the RAM 103 determined by the timing counter 106, along with the number of the contractions stored in the contraction counter 105. At this time, the timing counter 106 is indexed to the next memory address, and the contraction counter is reset to zero, to begin monitoring of the next sampling period.

An alarm unit 107 is connected to the contraction counter 105 via a limit value sensor 107a. Also connected to the limit value sensor is a limit value reference 107b, which is preset to contain a predetermined number value, for example five, at which the limit value sensor will actuate. The latter may be in the form of a conventional comparator. When the reference value is reached, an audible alarm 107c is energized, signalling the patient that her condition requires medical evaluation.

To advantage, the system of FIG. 5 is provided with a data interface 111, which can be connected via a modem 112 and telephone line 113 to a remote computer, for example, for evaluation by the physician at his office.

The system of FIG. 5 is incorporated in a small casing, such as reflected in FIGS. 2-4. In use, the casing is strapped to the pregnant woman, in the manner previously described, with the straps being appropriately adjusted so that the pressure of uterine contractions can be properly sensed.

The procedure and apparatus of the invention makes it possible in a practical way for pregnant women to be monitored for advance warning of the conditions of possible of premature birth, at a time when it is still possible to take corrective steps to prolong the pregnancy for many subjects. It has been known for some time that women susceptible to giving premature birth exhibit characteristic symptoms of uterine contraction patterns that are distinctly different from women likely to give birth at full term. However, the difficulty in taking advantage of this knowledge in actual practice arises from the requirement that the pattern of uterine contractions be monitored over a relatively long period of time. For cost and other reasons, it is not practical to conduct the necessary observations in a hospital or clinical environment. At the same time, attempts to carry on such monitoring in the home have been quite impractical, either because of the limitations of the equipment, on one hand, or its cost and complication on the other.

Pursuant to the procedure of the present invention, however, the patient can be monitored over a relatively long term, with a simple and inexpensive home device, by providing for continuous monitoring of uterine contractions (or periodic monitoring on a regular, daily basis) over a significant period of time, but only recording and processing the significant data. In particular, the procedure according to the invention takes note of and stores for further processing those uterine contractions which exceed a predetermined threshold level of intensity and which are continued for a predetermined threshold period of time. All others are ignored. By thus limiting what data is stored, the memory requirements of the monitoring equipment may be kept at a minimum, suitable for a device of moderate cost for home use.

On the knowledge that a certain frequency of significant contractions is characteristic of possible premature birth, the apparatus of the invention incorporates an automatic audible alarm which is activated in response to the detection of the predetermined number of "significant" contractions in a given time period, typically more than four per hour.

Although the apparatus and procedure of the invention monitors and responds to the intensity and duration of contractions, no data is recorded and stored relating to such duration or intensity. This significantly reduces the memory storage requirements of the device and enables the device to perform the critical function of monitoring over an extended period of time. At the same time, the effectiveness of the device in providing the desired early warning of potential premature birth is not compromised.

It should be understood, of course, that the specific forms of the invention herein illustrated and described are intended to be representative only, as certain changes may be made therein without departing from the clear teachings of the disclosure. Accordingly, reference should be made to the following appended claims in determining the full scope of the invention.

We claim:

1. Apparatus for monitoring a pregnancy for early detection of conditions characteristic of premature birth, which comprises
   (a) an instrument housing and a pressure sensitive transducer means for sensing pressures resulting from uterine contractions contained within said housing,
   (b) means adapted for retaining said housing and transducer means in sensing position on the abdomen of an expectant mother,
   (c) transducer circuit means in said housing for generating analog voltage signals according to pressures sensed by said transducer means,
   (d) A/D circuit means in said housing for converting said signals to digital form,
   (e) selection circuit means in said housing for automatically identifying and counting those digital signals representative of significant uterine contractions having an intensity greater than a predetermined threshold level and continuing for a duration greater than a predetermined duration while not counting contractions of lesser intensity or duration,
   (f) timing circuit means in said housing associated with said selection circuit means for providing the time of occurrence of the significant contractions,
   (g) memory means in said housing for the storage of data relating to the number of significant contractions and times of occurrence thereof, and
   (h) means in said housing for indicating the number of significant contractions sensed when said number exceeds a predetermined rate for a given unit of time.

2. An apparatus according to claim 1, further comprising
   a resettable counter circuit means in said housing for registering the number of significant contractions sensed by said transducer means,
   and wherein said timing circuit means includes timing means acting at the end of a predetermined monitoring period to store in said memory means (i) the count registered by said counter circuit and (ii) a time representing said monitoring period and
   acting at the end of a monitoring period to reset said counter circuit means and to index to a new address of said memory means.

3. Apparatus for monitoring a pregnancy for early detection of conditions characteristic of premature birth, which comprises
   (a) an instrument housing and a pressure sensitive transducer means for sensing pressures resulting from uterine contractions contained within said housing,
   (b) means adapted for retaining said housing and transducer means in sensing position on the abdomen of an expectant mother,
   (c) transducer circuit means for generating analog voltage signals according to pressures sensed by said transducer means,
   (d) A/D circuit means for converting said signals to digital form,
   (e) selection circuit means for identifying and counting those digital signals representative of significant uterine contractions of an intensity greater than a predetermined threshold level and continuing for a duration greater than a predetermined duration,
   (f) timing circuit means associated with said selection circuit means for providing the time of occurrence of the significant contractions,
   (g) memory means for the storage of data relating to the number of significant contractions and times of occurrence thereof, and
   (h) means for indicating the number of significant contractions served, when said number exceeds a predetermined rate for a given unit of time,
   (i) a resettable counter circuit means for registering the number of significant contractions sensed by said transducer means,
   (j) said timing circuit means including timing means acting at the end of a predetermined monitoring period to store in said memory means (i) the count registered by said counter circuit and (ii) a time representing said monitoring period,
   (k) said timing means further acting at the end of a monitoring period to reset said counter circuit means and to index to a new address of said memory means, and (l) an alarm device, (m) alarm circuit means connected to said counter circuit means and functioning when said counter circuit means registers a count greater than a predetermined number to actuate said alarm device.

4. Apparatus for monitoring a pregnancy for early detection of conditions characteristic of premature birth, which comprises (a) an instrument housing and a pressure sensitive transducer means for sensing pressures resulting from uterine contractions contained within said housing, (b) means adapted for retaining said housing and transducer means in sensing position on the abdomen of an expectant mother, (c) transducer circuit means for generating analog voltage signals according to pressures sensed by said transducer means, (d) A/D circuit means for converting said signals to digital form, (e) selection circuit means for identifying and counting those digital signals representative of significant uterine contractions of an intensity greater than a predetermined threshold level and continuing for a duration greater than a predetermined duration, (f) timing circuit means associated with said selection circuit means for providing the time of occurrence of the significant contractions, (g) memory means for the storage of data relating to the number of significant contractions and times of occurrence thereof, and (h) means for indicating the number of significant contractions sensed, when said number exceeds a predetermined rate for a given unit of time, (i) a resettable counter circuit means for registering the number of significant contractions sensed by said transducer means, (j) said timing circuit means including timing means acting at the end of a predetermined monitoring period to store in said memory means (i) the count registered by said counter circuit and (ii) a time representing said monitoring period, (k) said timing means further acting at the end of a monitoring period to reset said counter circuit means and to index to a new address of said memory means, (l) first and second indicator elements mounted on said housing and visible by the wearer, and (m) circuit means connecting said indicator elements to said transducer means and operative to actuate one of said indicator element upon sensing of pressures below a lower limit value and to actuate the other indicator element upon sensing of pressures above an upper limit value.

5. The process of monitoring a pregnancy for early detection of conditions characteristic of premature birth, which comprises (a) sensing uterine contractions of a pregnant woman and generating an electrical signal proportional to the intensity of such contractions over the periods of time during which they continue, (b) converting the electrical signal information to digital data, (c) comparing the intensity level of each such contraction, as indicated by the measured data, with a predetermined threshold level of intensity, (d) comparing the duration of each such contraction, as indicated by the measured data, with a predetermined minimum time duration interval, (e) selectively storing data only for the significant contractions whose intensity exceeds the predetermined threshold and whose duration exceeds the predetermined minimum duration interval, while ignoring data for other contractions, (f) continuing said sensing, converting, comparing and selective storing throughout a predetermined monitoring period, (g) throughout the monitoring period determining whether a predetermined number of selectively stored data items has been stored within a given time interval and providing an indication when said number is exceeded.

6. A process according to claim 1, wherein
the selectively stored data comprises for each contraction recorded, the fact of its occurrence, without regard to its duration or intensity, and the time of its occurrence.

7. A process according to claim 1, wherein said sensing step includes
continuously sensing said contractions throughout said monitoring period, and
said storing step includes storing, during said monitoring period, data relating to significant contractions sensed during successive predetermined sampling periods within said monitoring period.

8. A process according to claim 7, wherein said significant contractions, as determined by considerations of intensity and duration, are counted throughout each sampling period, storing values for (i) the count of significant contractions and (ii) the time of the sampling period, and providing an alarm indication if, during a sampling period, the number of significant contractions exceeds a predetermined number.

* * * * *